(12) United States Patent
Pham

(10) Patent No.: US 6,362,308 B1
(45) Date of Patent: Mar. 26, 2002

(54) ACID END GROUP POLY(D,L-LACTIDE-CO-GLYCOLIDE) COPOLYMERS HIGH GLYCOLIDE CONTENT

(75) Inventor: Chiem V. Pham, Mason, OH (US)

(73) Assignee: Alkermes Controlled Therapeutics Inc. II, Cambridge, MA (US)

(*) Notice: Subject to any disclaimer, the term of this patent is extended or adjusted under 35 U.S.C. 154(b) by 0 days.

(21) Appl. No.: 09/635,677

(22) Filed: Aug. 10, 2000

(51) Int. Cl.⁷ .............................................. C08G 63/08
(52) U.S. Cl. .................. 528/354; 528/355; 528/357; 528/358; 528/361; 525/408; 525/411
(58) Field of Search ............................... 528/354, 355, 528/357, 358, 361; 525/408, 411

(56) References Cited

U.S. PATENT DOCUMENTS

| | | | |
|---|---|---|---|
| 4,157,437 A | 6/1979 | Okuzumi et al. | 528/354 |
| 4,677,191 A | 6/1987 | Tanaka | 528/361 |
| 4,719,246 A | 1/1988 | Murdoch et al. | 521/134 |
| 4,767,628 A | 8/1988 | Hutchinson | 424/426 |
| 4,797,468 A | 1/1989 | De Vries | 528/354 |
| 4,849,228 A | 7/1989 | Yamamoto et al. | 424/457 |
| 4,859,763 A | 8/1989 | Takayanagi et al. | 528/357 |
| 5,134,122 A | 7/1992 | Orsolini | 514/15 |
| 5,192,741 A | 3/1993 | Orsolini et al. | 514/12 |
| 5,320,624 A | 6/1994 | Kaplan et al. | 606/77 |
| 5,478,921 A | 12/1995 | Roby et al. | 528/480 |
| 5,641,501 A | 6/1997 | Cooper et al. | 424/426 |
| 5,650,173 A | 7/1997 | Ramstack et al. | 424/489 |
| 5,654,008 A | 8/1997 | Herbert et al. | 424/489 |
| 5,705,197 A | 1/1998 | Van Hamont et al. | 424/501 |
| 5,770,231 A | 6/1998 | Mesens et al. | 424/497 |
| 5,792,477 A | 8/1998 | Rickey et al. | 424/501 |
| 5,817,343 A | 10/1998 | Burke | 424/489 |
| 5,876,761 A | 3/1999 | Bodmer et al. | 424/501 |
| 5,916,598 A | 6/1999 | Rickey et al. | 424/501 |
| 5,942,253 A | 8/1999 | Gombotz et al. | 424/501 |
| 5,945,128 A | 8/1999 | Deghenghi | 424/501 |
| 5,952,405 A | 9/1999 | Schoenberg et al. | 524/81 |
| 5,965,168 A | 10/1999 | Mesens et al. | 424/497 |
| 5,968,543 A | 10/1999 | Heller et al. | 424/425 |
| 6,004,573 A | 12/1999 | Rathi et al. | 424/426 |
| 6,007,565 A | 12/1999 | Roby et al. | 606/228 |

FOREIGN PATENT DOCUMENTS

| | | |
|---|---|---|
| EP | 0275 581 B1 | 8/1992 |
| EP | 0299 730 B1 | 10/1995 |

OTHER PUBLICATIONS

Wang et al., "Synthesis, characterization, biodegradation, and drug delivery application of biodegradable lactic/glycolic acid oligomes: I. Synthesis and characterization," J. Biomater. Sci. Polymer Edn. 8 (12): 905–17 (1997).

Kulkarni et al., "Biodegradable Poly(lactic acid) Polymers," J. Biomed. Mater. Res. 5:169–81 (1971).

Wang et al., Synthesis, characterization, biodegradation, and drug delivery application of biodegradable lactic/glycolic acid oligomes: Part II. Biodegradation and drug delivery application. J. Biomater. Sci. Polymer Edn. 9(1): 75–87 (1997).

Gilding et al., "Biodegradable polymers for use in surgery–polyglycolic/poly(lactic acid) homo– and copolymers: 1," Polymer 20:1459–1464 (1979).

Lewis, D. H., "Biodegradable Polymers as Drug Delivery Systems," (Chasin et al., eds) (Marcel Dekker, Inc., NY, 1990). Chapter 1, (1–41).

Tae Gwan Park, "Degradation of poly(lactic–co–glycolic acid) microspheres: effect of copolymer composition," *Biomaterials* 16:1123–30 (1995).

Bendix, "Analytical Studies on the Solubility Problem of Poly(D,L–Lactide–Co–Glycolide), 50:50," Proceed. Intern. Symp. Control. Rel. Bioact. Mater. 17:248–49. (1990).

March, Jerry, "*Advanced Organic Chemistry: Reactions, Mechanisms, and Structure,*" Second Edition (International Student Edition), McGraw–Hill Kogakusha, Ltd. (720–725).

Primary Examiner—P. Hampton-Hightower
(74) Attorney, Agent, or Firm—Andrea G. Reister; Covington & Burling

(57) ABSTRACT

Copolymers of lactide and glycolide with high glycolide content. The average glycolate block length is less then about 3, which allows the copolymer to be soluble in slightly polar solvents such as methylene chloride.

21 Claims, No Drawings

ACID END GROUP POLY(D,L-LACTIDE-CO-GLYCOLIDE) COPOLYMERS HIGH GLYCOLIDE CONTENT

BACKGROUND OF THE INVENTION

1. Field of the Invention

This invention relates to polymers of lactide and glycolide. More particularly, this invention relates to copolymers of lactide and glycolide having high glycolide content.

2. Related Art

Polymers of lactide and glycolide, and copolymers thereof, have long been known for their susceptibility to degradation by ester hydrolysis in aqueous environments. This property of these polymers has made them attractive for such medical applications as biodegradable surgical sutures; biodegradable rods, pins, and films for setting bone fractures; and as biodegradable polymer matrices for sustained, controlled active agent delivery. Consequently, research has been conducted into the manipulation of the polymers' degradation properties in order to control degradation times and active agent release rates.

Copolymers of lactide and glycolide have lactate and glycolate monomers. Polymers of lactate and glycolate can be obtained by polycondensation of lactic acid and glycolic acid with or without a catalyst (see, e.g., U.S. Pat. No. 4,157,437, the entirety of which is incorporated herein by reference); however, higher molecular weight polymers (i.e., those with molecular weights greater than a few thousand daltons) can be produced by starting with lactide and glycolide, which are the dioxane dimers of the acids. Production methods of lactide and glycolide are well known in the art (see Sorensen et al., *Preparative Methods of Polymer Chemistry*, Wiley, N.Y. (1968) and U.S. Pat. No. 4,797,468, both incorporated in their entireties herein by reference). One such method takes polymers of lactate obtained by polycondensation of lactic acid, and decomposes them under heat and reduced pressure, producing lactide (3,6-dimethyl-1,4-dioxane-2,5-dione, formula I):

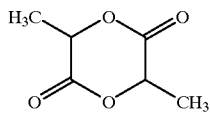

Similar methods are known to those skilled in the art for the production of glycolide (1,4-dioxane-2,5-dione, formula II):

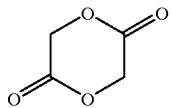

Use of glycolide and lactide as starting materials for the polymerization allows the synthesis of polymers with greater molecular weights than can be synthesized using glycolic acid and lactic acid as starting materials. The ring-opening polymerization reactions can be carried out in bulk or in solution. The polymerization is allowed to proceed for several hours at temperatures between about 150° C. and 250° C. if done in bulk (above the melting points of the monomers and the polymer to be synthesized), and at significantly lower temperatures (~50° C.) if done in solution. The polymerization proceeds under a reduced pressure of around 1–10 mm Hg or with a dry gas purge (e.g., nitrogen or argon), and in the presence of a catalyst (0.001 to 1% by weight) and a polymerization regulator (0.01 to 0.22 mol % of the monomer) (see, e.g., U.S. Pat. Nos. 4,157,437; 4,797,468; 4,767,628; 4,849,228; 4,859,763; 5,320,624; 5,952,405; 5,968,543; 6,004,573; 6,007,565; Wang et al., J. Biomater. Sci. Polymer Edn. 8(12): 905–17 (1997) (herein referred to as Wang et al., part I); Wu, *Encyclopedic Handbook of Biomaterials and Bioengineering* (Donald L. Wise, ed.) (Marcel Dekker, Inc., N.Y. 1995) (herein referred to as Wu), all of which are incorporated herein by reference in their entireties). Lewis acids are used to catalyze the polymerization, and stannous octoate (stannous 2-ethylhexanoate) is the most commonly used catalyst (U.S. Pat. No. 4,677,191, the entirety of which is incorporated herein by reference, reports copolymerization of lactic acid and glycolic acid in the absence of a catalyst). Typical polymerization regulators include monohydric, aliphatic, straight chain alcohols.

The copolymerization reaction can be represented symbolically as follows:

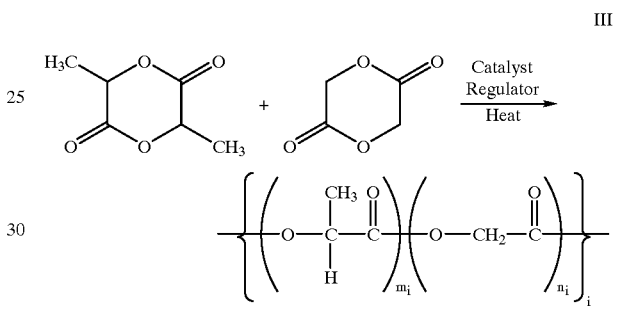

where i represents an oligomer within the polymer containing $m_i$ lactate units and $n_i$ glycolate units; $m_i$ and $n_i$ are the block lengths of lactate and glycolate within the $i^{th}$ oligomer. For a polymer composed of N such oligomers, the sum of $m_i$ and $n_i$ over all of the oligomers i, divided by N gives the average block lengths of lactate units and glycolate units respectively. The average block lengths of lactate and glycolate can be measured using $^{13}$C-NMR techniques known to those skilled in the art. The lactide/glycolide mole ratio can be measured using proton NMR techniques known to those skilled in the art.

The molecular weight of a copolymer of lactide and glycolide is one of the characteristics determinative of its degradation rate, with lighter copolymers having greater degradation rates than heavier copolymers (see Wang et al., J. Biomater. Sci. Polymer Edn. 9(1): 75–87 (1997) (herein referred to as Wang et al. part II), the entirety of which is herein incorporated by reference). One method known to those skilled in the art for determining the molecular weights of polymers is to measure their intrinsic viscosity in a solvent of the polymers, where greater intrinsic viscosity corresponds to a greater molecular weight.

Glycolide is more amenable to addition to a growing polymer chain than is lactide (see Gilding et al., Polymer 20: 1459–1464 (1979) (herein referred to as Gilding et al.), the entirety of which is incorporated herein by reference). Gilding et al. report that glycolide is three times more likely to be added to the end of a polymer than lactide if the growing group is a glycolide, and five times more likely if the growing group is a lactide. Therefore, all else being equal, the polymerization reaction will naturally favor copolymers with high glycolide content and blocks of glycolide separated by single lactide units (see Wu).

Glycolide-rich copolymers (i.e., copolymers of lactide and glycolide containing at least 50 mol. % glycolide) degrade faster than lactide-rich copolymers. (see U.S. Pat. No. 4,156,437; Lewis, *Biodegradable Polymers as Active agent Delivery Systems* (Chasin et al., eds.) (Marcel Dekker, Inc., N.Y. 1990) (herein referred to as Lewis); Park, Biomaterials 16: 1123–30 (1995) (herein referred to as Park), the entirety of each of which is incorporated herein by reference). It has been hypothesized that these greater degradation rates of glycolide-rich copolymers relative to lactide-rich copolymers stems from the hydrophilicity of glycolic acid relative to lactic acid (lactic acid contains a non-polar methane group, making it more hydrophobic) (see, e.g., Wang et al. part II). The greater hydrophilicity of glycolic acid allows the polymer to hydrate more easily, thus allowing access to the ester bonds of the polymer backbone by water. Since degradation of the polymer occurs by hydrolysis of the ester bonds, water's easier access to the ester bonds results in a more rapid degradation of the polymer (see Park). However, along with the ease of hydration of glycolide-rich copolymers comes another consequence of glycolide's hydrophilicity: the difficulty of dissolving the glycolide-rich copolymer in slightly polar solvents such as methylene chloride. This difficulty must be overcome in order to use glycolide-rich copolymers in the production of active agent-loaded microparticles.

A significant problem with lactide/glycolide copolymers with high glycolide content is their low solubility in slightly polar solvents such as methylene chloride (see Bendix, Proceed. Intern. Symp. Control. Rel. Bioact. Mater. 17:248–49 (1990) (referred to herein as Bendix), the entirety of which is incorporated herein by reference; see also Wu and Gilding et al.). This problem prevents use of standard solution polymerization and standard purification techniques. An example of a standard purification technique is to dissolve the polymer in methylene chloride and then to pour the polymer solution into methanol. The polymer precipitates, leaving impurities such as unreacted monomers, catalyst and regulator behind. For copolymers rich in glycolide, the choices of polymer solvents (methylene chloride in the example) and polymer non-solvents (methanol in the example) is limited. (For another approach to purifying the polymer, see U.S. Pat. No. 4,849,228, the entirety of which is incorporated herein by reference.) These limitations caused by the insolubility of glycolide-rich copolymers in slightly polar solvents are significant not only to the problems of polymerization and purification, but are also strongly felt in attempts to use these copolymers as matrices for controlled release of active agents because many of the techniques for making controlled release formulations require the polymer to be dissolved in a slightly polar solvent. Thus, there is a need in the art for a glycolide-rich copolymer that can be readily dissolved in slightly polar solvents, such as methylene chloride.

SUMMARY OF THE INVENTION

The present invention relates to copolymers of lactide and glycolide with high glycolide content (at least 50% glycolide) that are soluble up to about 40% (m/v) in methylene chloride, and to methods of making these copolymers. In one aspect of the invention, a copolymer having 40–50 mole percent lactide and 50–60 mole percent glycolide is provided that is soluble in methylene chloride in an amount greater than about 10%. In another aspect of the invention, the high glycolide content copolymer has an average glycolate block length of less than about 3. In a further aspect of the invention, the high glycolide content copolymer has an inherent viscosity in chloroform of between 0.07–0.5 dL/g.

Another aspect of the present invention provides block copolymers comprising the glycolide-rich copolymers of glycolide and lactide of the present invention and another polymer or copolymer. These block co-polymers can be tailored to have specific mechanical and degradation properties through selection of the other polymer or copolymer.

Another aspect of the present invention provides graft copolymers comprising the glycolide-rich copolymers of glycolide and lactide of the present invention grafted to the backbone of another polymer or copolymer. These graft co-polymers can be tailored to have specific mechanical and degradation properties through selection of the other polymer or copolymer.

Another aspect of the present invention provides a sustained release active agent delivery system comprising a high glycolide content copolymer that is a biodegradable matrix for an active agent. A wide range of active agents can be incorporated into controlled release devices using the copolymers of the present invention. Preferred active agents for use with the copolymers of the present invention include human growth hormone (hGH), luteinizing hormone releasing hormone (LHRH), and analogs of LHRH, insulin, anti-inflammatory compounds, and anesthetic compounds. A further aspect of the invention is an active agent delivery system wherein the high glycolide copolymer is dissolved in methylene chloride during the preparation process.

The present invention also provides a method of making high glycolide content copolymers comprising making a mixture comprising D,L-lactide, glycolide, glycolic acid and stannous octoate, and heating the mixture to a temperature between about 175° C. and about 220° C. Alternatively, instead of the racemic D,L-lactide, optically active L-lactide or D-lactide may be substituted. In a further aspect of the invention, glycolic acid is present in the reaction mixture in an amount of about 0.3% to about 5% of the total monomer weight. In yet a further aspect of the invention, stannous octoate is present in the reaction mixture in an amount of about 0.005% to about 0.06% of the total monomer weight. In a still further aspect of the invention, D,L-lactide is present in an amount between about 40% and 50%, and glycolide is present in an amount between about 50% and 60% of the total monomer weight.

Features and Advantages

A feature of the present invention is that the copolymers of lactide and glycolide have a high glycolide content, and therefore also have the accompanying degradation properties of a high glycolide content copolymer. Yet these copolymers have the advantage over other high-glycolide copolymers of being substantially soluble in slightly polar solvents. This allows the copolymers to be used in the most common methods for producing sustained release active agent/polymer microparticles.

DETAILED DESCRIPTION OF THE PREFERRED EMBODIMENTS

The present invention relates to acid end-group copolymers of lactide and glycolide with a glycolide content of at least about 50% that are soluble in slightly polar solvents such as methylene chloride in an amount between about 10–40%, preferably in an amount between about 20%–40%, and more preferably in an amount between about 30%–40%. The unexpected enhanced solubility of these copolymers relative to high glycolide copolymers of the prior art is rooted in their short glycolate block length. Glycolate blocks are interrupted by lactate blocks before the glycolate block grows beyond about 3. Therefore, the present invention provides high-glycolide content copolymers of glycolide and lactide with average glycolate block lengths of less than about 3.

By "slightly polar solvents" or "moderately polar solvents" is meant those solvents that have a polarity intermediate between highly polar solvents such as water and non-polar solvents such as mineral oil. Examples of slightly polar solvents include, but are not limited to, methylene chloride, chloroform, ethyl acetate, methyl acetate, N-methyl 2-pyrrolidone, 2-pyrrolidone, propylene glycol, tetrahydrofuran (THF), acetone, oleic acid, methyl ethyl ketone and mixtures thereof As would be apparent to one skilled in the art, in a range from low to high of slightly polar solvents, THF would be considered at the low end, and ethyl acetate and acetone would be considered at the high end. Quantitative values for solvent polarity are described in March, Jerry, *Advanced Organic Chemistry: Reactions, Mechanisms, and Structure*, Second Edition (International Student Edition), McGraw-Hill Kogakusha, Ltd., the entirety of which is incorporated herein by reference. As discussed in Chapter 10 of the foregoing, one measure of solvent polarity is a "Z Value," transition energies calculated from the position of the charge-transfer peak in the UV spectrum of the complex between iodide ion and 1-methyl- or 1-ethyl-4-carbomethoxypyridinium ion. Another scale is based on the position of electronic spectra peaks of the pyridinium-N-phenolbetaine in various solvents (see Dimroth, Reichardt, Siepmann, and Bohlmann, *Justus Liebergs Ann. Chem.* 661, 1 (1963); Dimroth and Reichardt, *Justus Liebergs Ann. Chem.* 727, 93 (1969)). Solvent polarity values on this scale are called $E_T$ values, which are related to Z values by the expression:

$$Z=1.41E_T+6.92$$

Slightly or moderately polar solvents have an $E_T$ value between about 37 and 43.

Quantitative solubility data for nonpolar organic compounds may be calculated from the Hildebrand expression for the square root of the cohesive energy density which is defined as the solubility parameter ($\delta$). The dimensions for $\delta$ are $(cal\ cm^{-3})^{1/2}$, but the Hildebrand unit (H) is used for convenience. $\delta$ values are most useful for nonpolar solvents. Some consideration must be given to the dipole-dipole interactions in more polar solvents. Moderately polar solvents typically have a solubility parameter ($\delta$) in the range of from about 7 to about 14.5 in Hildebrand units (H).

The copolymers of the present invention are made from lactide and glycolide monomers, with a Lewis acid catalyst, preferably stannous octoate. A polymerization regulator such as an alpha hydroxy carboxylic acid or an aliphatic alcohol is used to regulate the molecular weights of the polymers. The preferred polymerization regulator is glycolic acid, which adds to the ends of the polymer and provides the acid end groups. The reaction is carried out under dry (water free) conditions: under a vacuum, or under a dry gas, such as nitrogen or argon, preferably under nitrogen. The reaction is carried out at a temperature between about 175° C. and about 220° C., preferably between about 180° C. and about 190° C., and most preferably at about 180° C. The reaction is allowed to proceed for between 1 and 48 hours, preferably between 10 and 35 hours, and most preferably for about 24 hours.

The copolymers of the present invention are preferably used to prepare microparticles. In a particularly preferred embodiment, the copolymers are used to prepare microparticles for the controlled sustained release of active agents.

By "active agent" is meant an agent, drug, compound, composition of matter or mixture thereof which provides some pharmacological, often beneficial, effect. This includes foods, food supplements, nutrients, drugs, vitamins, and other beneficial agents. As used herein, the terms further include any physiologically and pharmacologically active substance that produces a localized or systemic effect in a patient. Such active agents include antibiotics, antiviral agents, anepileptics, analgesics, anti-asthmatics, anti-inflammatory agents and bronchodilators, and may be inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, tranquilizers, anticonvulsants, muscle relaxants, anti-Parkinson agents, analgesics, anti-inflammatories, muscle contractants, antimicrobials, antimalarials, hormonal agents including contraceptives, sympathomimetics, polypeptides and proteins capable of eliciting physiological effects, diuretics, lipid regulating agents, antiandrogeic agents, leukotriene antagonists, antiparasites, neoplastics, antineoplastics, hypoglycemics, nutritional agents and supplements, growth supplements, fats, ophthalmics, antienteritis agents, electrolytes and diagnostic agents. Particularly preferred active agents include human growth hormone (hGH), luteinizing hormone releasing hormone (LHRH), and analogs of LHRH, insulin, anti-inflammatory compounds, and anesthetic compounds.

EXAMPLES

The following examples are provided to explain the invention, and to describe the materials and methods used in carrying out the invention. The examples are not intended to limit the invention in any manner.

Example 1

Preparation of a 45:55 Poly-D,L-lactide-co-glycolide with a MW of 7 kD

In a 250-ml flask equipped with a stirrer paddle, stirrer motor and a gas outlet, 26.7 grams of D,L-lactide, 23.3 grams of glycolide, 2.5 g glycolic acid and 18 mg of stannous octoate were placed under nitrogen blanket. The reaction flask was purged with dry nitrogen by evacuating and releasing the vacuum five times. The flask and its contents were lowered into a silicon oil bath, preheated to a temperature of 180° C., and heated under stirring in a nitrogen atmosphere. Twenty four hours later, vacuum was applied for thirty minutes to remove the unreacted monomers. The resulting polymer was collected by extruding into liquid nitrogen and milled in a Retsch mill. The yield of the copolymer obtained was 39.2 grams (78.4%). The inherent viscosity of this copolymer was 0.10 dL/g measured in chloroform at 30° C. The polymer was soluble in methylene chloride at a concentration up to 40%. The average glycolate block length determined by $^{13}$C-NMR was 2.8. The lactide/glycolide mole ratio determined by proton NMR was 45:55. The weight-averaged molecular weight was 7kD as measured by gel permeation chromatography using chloroform as the mobile phase and polystyrene standards.

Example 2

Preparation of a 45:55 Poly-D,L-lactide-co-glycolide with a MW of 12 kD

In a 500-ml flask equipped with a stirrer paddle, stirrer motor and a gas outlet, 221.8 grams of D,L-lactide, 193.6 grams of glycolide, 8.3 g glycolic acid and 126 mg of stannous octoate were placed under nitrogen blanket. The reaction flask was purged with dry nitrogen by evacuating and releasing the vacuum five times. The flask and its contents were lowered into a silicon oil bath, preheated to a temperature of 180° C., and heated under stirring in a nitrogen atmosphere. Twenty four hours later, vacuum was applied for thirty minutes to remove the unreacted monomers. The resulting polymer was collected by extruding into liquid nitrogen and milled in a Retsch mill. The yield of the copolymer obtained was 364.0 grams (87.6%). The inherent viscosity of this copolymer was 0.15 dL/g measured in chloroform at 30° C. The polymer was soluble in methylene chloride at a concentration up to 40%. The glycolate block length determined by $^{13}$C-NMR was 2.9. The lactide/glycolide mole ratio determined by proton NMR was 46:54. The weight-averaged molecular weight was 12kD as measured by gel permeation chromatography using chloroform as the mobile phase and polystyrene standards.

Example 3

Preparation of a 48:52 Poly-D,L-lactide-co-glycolide with a MW of 7 kD

In a 250-ml flask equipped with a stirrer paddle, stirrer motor and a gas outlet, 29.2 grams of D,L-lactide, 20.8 grams of glycolide, 2.5 g glycolic acid and 16 mg of stannous octoate were placed under nitrogen blanket. The reaction flask was purged with dry nitrogen by evacuating and releasing the vacuum five times. The flask and its contents were lowered into a silicon oil bath, preheated to a temperature of 180° C., and heated under stirring in a nitrogen atmosphere. Twenty four hours later, vacuum was applied for thirty minutes to remove the unreacted monomers. The resulting polymer was collected by extruding into liquid nitrogen and milled in a Retsch mill. The yield of the copolymer obtained was 39.9 grams (79.8%). The inherent viscosity of this copolymer was 0.10 dL/g measured in chloroform at 30° C. The polymer was soluble in methylene chloride at a concentration up to 40%. The glycolate block length determined by $^{13}$C-NMR was 2.8. The lactide/glycolide mole ratio determined by proton NMR was 49:51. The weight-averaged molecular weight was 7kD as measured by gel permeation chromatography using chloroform as the mobile phase and polystyrene standards.

Example 4

Preparation of Block Copolymers Comprising High Glycolide Content Copolymers of Lactide and Glycolide with Good Solubility in Methylene Chloride and Other Polymers or Copolymers.

High glycolide content copolymers of lactide and glycolide with good solubility in methylene chloride are prepared in accordance with Examples 1–3 above. The copolymers are blended with homopolymers of lactide or glycolide (see Kulkarni et al., J. Biomed. Mater. Res. 5: 169–81 (1971); U.S. Pat. Nos. 4,719,246 and 6,007,565 the entirety of each of which is herein incorporated by reference), or with polycaprolactone or polytrimethylene carbonate or copolymers thereof in order to make block copolymers with superior mechanical properties (see U.S. Pat. No. 5,320,624, the entirety of which is incorporated herein by reference). High glycolide content copolymers of lactide and glycolide with good solubility in methylene chloride are prepared in accordance with Examples 1–3 above. The copolymers are blended with poly(ϵ-caprolactone) and poly(p-dioxanone) to produce a block copolymer that has better molding characteristics than the lactide/glycolide copolymer alone (see U.S. Pat. No. 5,641,501, the entirety of which is incorporated herein by reference). High glycolide content copolymers of lactide and glycolide with good solubility in methylene chloride are prepared in accordance with Examples 1–3 above. The copolymers are used to enhance the biodegradability of less biodegradable polymers by forming block copolymers (see U.S. Pat. No. 5,968,543, the entirety of which is incorporated herein by reference). High glycolide content copolymers of lactide and glycolide with good solubility in methylene chloride are prepared in accordance with Examples 1–3 above. The copolymers are combined with polyethylene glycol, resulting in a block copolymer with reverse thermal gelation properties, changing phase from a liquid to a gel upon warming from room temperature to body temperature (see U.S. Pat. No. 6,004,573, the entirety of which is incorporated herein by reference).

Example 5

Preparation of a Graft Copolymer Comprising a High Glycolide Content Copolymer of Lactide and Glycolide with Good Solubility in Methylene Chloride and a Backbone Polymer or Copolymer.

A backbone block copolymer is prepared from monomers of alkyl acrylate, alkyl methacrylate, ethylene or vinyl acetate forming one block, and monomers of 2-hydroxyethyl acrylate, 2-hydroxyethyl methacrylate, hydroxypropyl acrylate, 2-hydroxyethyl methacrylate, hydroxypropyl acrylate, hydroxypropyl methacrylate, allyl alchohol, or N-(t-butyl)aminoethyl methacrylate forming the second block, where the monomers of the second block are present in an amount of up to about 6% by weight. Glycolide and lactide are graft polymerized according to Examples 1–3 above onto the hydroxyl groups of the backbone polymer. (See U.S. Pat. No. 5,952,405, incorporated in its entirety herein by reference.)

Example 6

Preparation of Microparticles Comprising a High Glycolide Content Copolymer of Lactide and Glycolide with Good Solubility in Methylene Chloride and an Active Agent by Solvent Evaporation.

A solution is made of any of the polymers of the previous Examples and an active agent in a slightly polar solvent. Typically, the active agent is soluble in slightly polar solvents. Examples of preferred active agents are human growth hormone, luteinizing hormone releasing hormone, insulin, anti-inflammatory compounds and anesthetic compounds. The solution is then emulsified in water or other polar solvent, the solvent is removed under vacuum, and active agent-loaded microspheres are collected (see U.S. Pat. Nos. 5,916,598; 5,792,477; and 5,650,173, all incorporated herein by reference in their entireties).

Example 7

Preparation of Microparticles Comprising a High Glycolide Content Copolymer of Lactide and Glycolide with Good Solubility in Methylene Chloride and an Active Agent by Phase Separation.

A polymer of any of the previous Examples and an active agent, which is typically water soluble, are added to a slightly polar solvent. Examples of preferred active agents are human growth hormone, luteinizing hormone releasing hormone, insulin, anti-inflammatory compounds and anesthetic compounds. A non-solvent to both polymer and active agent, e.g., silicone oil, is added to the mixture and a coacervate is formed. The organic solvent is removed and the active agent-loaded microparticles are recovered from the non-solvent. (See Lewis).

Example 8

Preparation of Microparticles Comprising a High Glycolide Content Copolymer of Lactide and Glycolide with Good Solubility in Methylene Chloride and an Active Agent by Fluidized Bed Coating.

A polymer of any of the previous Examples and an active agent are dissolved in a slightly polar solvent. Examples of preferred active agents are human growth hormone, luteinizing hormone releasing hormone, insulin, anti-inflammatory compounds and anesthetic compounds. The solution is processed in a Wurster air suspension coater, known to those skilled in the art, and microparticles of the active agent and polymer are recovered (See Lewis).

Example 9

Preparation of Microparticles Comprising a High Glycolide Content Copolymer of Lactide and Glycolide with Good Solubility in Methylene Chloride and an Active Agent by Spray Drying.

A polymer of any of the previous Examples and an active agent are dissolved in a slightly polar solvent. Examples of preferred active agents are human growth hormone, luteinizing hormone releasing hormone, insulin, anti-inflammatory compounds and anesthetic compounds. The polymer is dissolved in methylene chloride, the active agent is either suspended or dissolved in the polymer solution, depending on its solubility in methylene chloride. The solution or the suspension is then injected through a nozzle, forming a spray. The solvent is evaporated, leaving active agent encapsulated within the polymer. (See, e.g., U.S. Pat. No. 5,942,253, incorporated herein by reference in its entirety).

Examples 10–16

Other Methods for Preparation of Microparticles Comprising a High Glycolide Content Copolymer of Lactide and Glycolide with Good Solubility in Methylene Chloride and an Active Agent.

Example 10

An aqueous solution of poly vinyl alcohol and an organic solution of any of the polymers of the previous Examples and an active agent in ethyl acetate and benzyl alcohol are made. The two solutions are passed through a static mixer with a faster flow rate for the aqueous solution than the organic. The emulsion formed after the mixer is quenched in water, from which the microparticles are separated and dried. (See U.S. Pat. Nos. 5,965,168 and 5,770,231, the entireties of which are herein incorporated by reference.)

Example 11

A solution of any of the polymers of the previous Examples in methylene chloride and an aqueous solution of an active agent are made. These are combined to make a water-in-oil emulsion. Polydimethylsiloxane is added, and the mixture is homogenized. Octamethylcyclotetrasiloxane is added to harden the microparticles, which are then collected (See U.S. Pat. No. 5,942,253, incorporated herein by reference in its entirety).

Example 12

An aqueous solution of an active agent is added to a solution of any of the polymers of the previous Examples in methylene chloride and an emulsion is made. To the emulsion is added an aqueous solution of gelatin. The methylene chloride is evaporated and active agent-loaded microspheres are recovered. (See U.S. Pat. No. 5,876,761, incorporated herein by reference in its entirety.)

Example 13

A solution of any of the polymers of the previous Examples in an organic solvent is made, and the active agent is suspended in the solution. The solvent is then removed, and the matrix is fragmented, resulting in active agent-loaded microparticles. (See U.S. Pat. No. 5,817,343, incorporated herein by reference in its entirety.)

Example 14

An active agent and sucrose are dissolved in acetonitrile, and a separate solution of any of the polymers of the previous Examples and acetonitrile is made. The solutions are combined, and oil with lecithin is added. The acetonitrile is evaporated, and the oil, active agent, sucrose and polymer are emulsified. The emulsion is added to an organic solvent, and the active agent-loaded microparticles are recovered. (See U.S. Pat. No. 5,705,197, incorporated herein by reference in its entirety.)

Example 15

Any of the polymers of the previous Examples is dissolved in dioxan, and an aqueous solution of the active agent is prepared. The solutions are combined and cast as a film, and the solvents are evaporated, leaving active agent-loaded polymer. Other methods do not require that the copolymer be dissolved in an organic solvent. (See U.S. Pat. No. 4,747,628, incorporated herein by reference in its entirety.)

Example 16

Any of the polymers of the previous Examples is ground up, and an aqueous slurry of an active agent, typically a polypeptide, is added. The mixture is dried, and the active agent-loaded copolymer is dried and extruded. (See U.S. Pat. No. 5,945,128, incorporated herein by reference in its entirety.)

CONCLUSION

While various embodiments of the present invention have been described above, it should be understood that they have been presented by way of example only, and not limitation. The breadth and scope of the present invention should not be limited by any of the above-described exemplary embodiments, but should be defined only in accordance with the following claims and their equivalents.

I claim:

1. A copolymer of D,L-lactide and glycolide comprising 40–50 mole percent lactide and 50–60 mole percent glycolide wherein the solubility of said copolymer in methylene chloride is greater than about 10% (m/v).

2. The copolymer of claim 1 wherein the average glycolate monomer block length is less than about 3.

3. The copolymer of claim 2 wherein the inherent viscosity of the copolymer in chloroform is 0.07–0.5 dL/g.

4. The copolymer of claims 1, 2, or 3, wherein the solubility of said copolymer in methylene chloride is between 30–40% (m/v).

5. A method of making a copolymer of D,L-lactide and glycolide comprising: making a mixture comprising D,L-lactide, glycolide, an hydroxy carboxylic acid, and stannous octoate and heating the mixture to a temperature of between about 175° C. and about 200° C. to form said copolymer.

6. The method of claim 5, wherein the mixture is heated to a temperature of between about 180° C. and about 190° C.

7. The method of claim 5, wherein the mixture is heated to a temperature of about 180° C.

8. The method of claim 5, wherein said hydroxy carboxylic acid is glycolic acid.

9. The method of claim 8, wherein said glycolic acid is present in the mixture in an amount of about 0.3% to about 5% of the total monomer weight.

10. The method of claim 5, wherein said stannous octoate is present in the mixture in an amount of about 0.005% to about 0.06% of the total monomer weight.

11. The method of claim 10, wherein said stannous octoate is present in the mixture in an amount of about 0.03%.

12. The method of claim 5, wherein the mixture is heated for a time of between about 6 and about 48 hours.

13. The method of claim 12, wherein the mixture is heated for about 24 hours.

14. The method of claim 5, wherein said D,L-lactide is present in the mixture in an amount between about 50% and about 60% of the total monomer weight.

15. The method of claim 5, wherein said heating step is carried out in an environment that is substantially free of water.

16. The method of claim 5, further comprising: collecting said copolymer.

17. The method of claim 16, wherein said collecting step comprises: extruding the copolymer into liquid nitrogen.

18. The method of claim 17, further comprising: milling said copolymer.

19. A copolymer of D,L-lactide and glycolide comprising 40–50 mole percent lactide and 50–60 mole percent glycolide wherein the average glycolate block length is less than about 3.

20. The copolymer of claim 19 wherein the inherent viscosity of said copolymer in chloroform is 0.07–0.5 dL/g.

21. The copolymer of claim 19 or 20, wherein the solubility of said copolymer in methylene chloride is between 30–40% (m/v).

* * * * *

Disclaimer 6,362,308 B1—Chiem V. Pham, Mason, OH. (US). ACID END GROUP POLY(D,L-LACTIDE-CO-GLYCOLIDE) COPOLYMERS HIGH GLYCOLIDE CONTENT. Patent dated Mar. 26, 2002. Disclaimer filed Aug. 14, 2003, by the assignee, Alkermes Controlled Therapeutics Inc. II.

Hereby enters this disclaimer to claim 1 and 4 of said patent.

*(Official Gazette, August 17, 2004)*